US012163936B2

(12) United States Patent
Geromanos et al.

(10) Patent No.: US 12,163,936 B2
(45) Date of Patent: Dec. 10, 2024

(54) METHODS, MEDIUMS, AND SYSTEMS TO COMPARE DATA WITHIN AND BETWEEN COHORTS

(71) Applicant: WATERS TECHNOLOGIES IRELAND LIMITED, Dublin (IE)

(72) Inventors: Scott J. Geromanos, Middletown, NJ (US); Steven J. Ciavarini, Natick, MA (US); Marisa Gioioso, Milford, MA (US); Ovidiu Pop, Milford, MA (US)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 613 days.

(21) Appl. No.: 17/238,540

(22) Filed: Apr. 23, 2021

(65) Prior Publication Data
US 2021/0333251 A1 Oct. 28, 2021

Related U.S. Application Data

(60) Provisional application No. 63/014,858, filed on Apr. 24, 2020.

(51) Int. Cl.
*G01N 30/88* (2006.01)
*G01N 30/72* (2006.01)
(Continued)

(52) U.S. Cl.
CPC .............. *G01N 30/88* (2013.01); *G01N 30/72* (2013.01); *G01N 30/8617* (2013.01);
(Continued)

(58) Field of Classification Search
CPC .... G01N 30/88; G01N 30/72; G01N 30/8617; G01N 2030/862; G01N 2030/8648; G01N 30/8672; G16C 20/20
See application file for complete search history.

(56) References Cited

U.S. PATENT DOCUMENTS 5,668,373 A  9/1997 Robbat et al.
6,717,130 B2  4/2004 Bateman et al.
(Continued)

FOREIGN PATENT DOCUMENTS

WO   2014116711 A1   7/2014

OTHER PUBLICATIONS

International Search Report and Written Opinion for International application No. PCT/IB2021/053381, mailed on Sep. 13, 2021, 19 pages.
(Continued)

*Primary Examiner* — Tung S Lau
(74) *Attorney, Agent, or Firm* — Goodwin Procter LLP

(57) ABSTRACT

Exemplary embodiments provide methods, mediums, and systems for analyzing spectrometry and/or chromatography data, and in particular to techniques to improve the reproducibility of results of spectrographic and/or chromatographic experiments. For example, some embodiments provide techniques for normalizing mass spectrometry (MS) and/or liquid chromatography (LC) data across different experimental devices, allowing data from different cohorts to be directly compared. To this end, exemplary embodiments provide a reliable, reproducible target library usable across different platforms, laboratories, and users. One embodiment leverages statistical techniques to select experimental parameters configured to reduce or minimize the chance of misidentifying a target molecule. Another embodiment leverages the law of large numbers to produce a composite product ion spectrum usable across different experiments. The composite product ion spectrum allows regression curves to be generated, where the regression curves can be used to normalize an experimental mass spectrum.

30 Claims, 8 Drawing Sheets

(51) Int. Cl.
*G01N 30/86* (2006.01)
*G16C 20/20* (2019.01)

(52) U.S. Cl.
CPC ....... *G16C 20/20* (2019.02); *G01N 2030/862* (2013.01); *G01N 2030/8648* (2013.01)

(56) References Cited

U.S. PATENT DOCUMENTS

| | | | | |
|---|---|---|---|---|
| 9,040,903 | B2* | 5/2015 | Coon | H01J 49/0027 |
| | | | | 250/281 |
| 10,593,530 | B2* | 3/2020 | Thoeing | H01J 49/0036 |
| 2006/0281134 | A1* | 12/2006 | Love | G01N 33/6842 |
| | | | | 435/7.1 |
| 2007/0009898 | A1* | 1/2007 | Geromanos | G01N 33/6848 |
| | | | | 702/19 |
| 2009/0006002 | A1* | 1/2009 | Honisch | C12Q 1/6872 |
| | | | | 702/20 |
| 2011/0093204 | A1* | 4/2011 | Zucht | G01N 33/9406 |
| | | | | 702/19 |
| 2018/0166265 | A1 | 6/2018 | Geromanos et al. | |

OTHER PUBLICATIONS

Stoev, G., and Michailova, A., "Quantitative assessment of the reliability of identification by high-performance liquid chromatography-mass spectrometry", Journal of Chromatography A 1031(1-2):11-16 (2004).

International Preliminary Report on Patentability for International Patent Application No. PCT/IB2021/053381, mailed Nov. 3, 2022.

* cited by examiner

METHODS, MEDIUMS, AND SYSTEMS TO COMPARE DATA WITHIN AND BETWEEN COHORTS

CROSS-REFERENCE TO RELATED APPLICATIONS

The present application is related to, and claims priority to, U.S. Provisional Patent Application No. 63/014,858, filed on Apr. 24, 2020 and entitled "Universal Workflow: Software to Enable Global Collaboration of Large Cohorts of LC-MS and LC-MS/MS Data."

BACKGROUND

In mass spectrometry (MS) or liquid chromatography/mass spectrometry (LC-MS) experiments, precursor ions are broken apart into product ions. The precursor and product ions are then analyzed in an attempt to identify them. The results of an MS or LC-MS experiment is generally a mass spectrum (a plot of a molecule's intensity versus its mass-to-charge ratio, as measured by an ion detector).

Problematically, the mass spectrum generated by MS or LC-MS devices can vary depending on the device's characteristics (such as age, calibration settings, ambient conditions, etc.), which can vary from laboratory-to-laboratory, user-to-user, and even experiment-to-experiment. Thus, comparing data across different acquisition events (even when generated on a single device) can be a daunting task. Because of this challenge, existing MS/LC-MS data processing software is generally restricted by sample type, instrument platform, and acquisition method.

BRIEF SUMMARY

A brief summary of exemplary embodiments will next be described. These examples may be embodied as methods, instructions stored on non-transitory computer-readable storage media, devices performing the described actions, etc. Unless otherwise noted, it is contemplated that the described embodiments may be used separately or together in any combination in order to achieve synergistic effects.

According to a first embodiment, a computing device may receive, via a user interface, a list of two or more target molecules to be identified in a sample for analysis by a mass spectrometry apparatus according to an experimental method defined by a plurality of parameters. The device may perform a statistical analysis based on the list of two or more target molecules, the statistical analysis configured to determine a probability of misidentifying one or more of the target molecules in the list. The device may select a set of values for the plurality of parameters that reduces the probability below a predetermined threshold value, and may present, on the user interface, the selected set of values.

According to a second embodiment that may be used in conjunction with the first embodiment, the statistical analysis may be performed based on a subset of target molecules in the list, the subset representing a group of relatively less common markers from among the target molecules.

According to a third embodiment that may be used in conjunction with any of the first through second embodiments, the plurality of parameters of the experimental method may include an elution position, a collisional cross section, a drift position, and/or a mass accuracy.

According to a fourth embodiment that may be used in conjunction with any of the first through third embodiments, the values for the plurality of parameters may be selected based on a known three-dimensional positioning of one of the target molecules, a known fragmentation pattern of one of the target molecules, and/or a known relationship between two of the target molecules.

According to a fifth embodiment that may be used in conjunction with any of the first through fourth embodiments, the computing device may present, on the user interface, a score representing a likelihood that a presence or absence of the two or more target molecules will be correctly identified in the sample given the selected set of values.

According to a sixth embodiment that may be used in conjunction with the fifth embodiment, the score may be computed by: (a) consulting a consensus library comprising immutable attributes of spectral features; (b) counting a frequency at which one of the target molecules is present in the consensus library; (c) transforming the frequency count into a probability score; repeating steps (a)-(c) for a plurality of the target molecules; and multiplying the probability scores for the plurality of target molecules together.

According to seventh embodiment that may be used in conjunction with the fifth or sixth embodiments, the score may be configured to increase as a function of a number of dimensions of separation available as determined by an acquisition method applied.

According to an eighth embodiment that may be used in conjunction with the fifth through seventh embodiments, the score may be configured to increase as a function of a resolving power of the mass spectrometry apparatus.

According to a ninth embodiment that may be used in conjunction with the fifth through eighth embodiments, the score may be computed based on a combination of the two or more target molecules' mass-to-charge ratio, retention time, and drift time.

According to a tenth embodiment that may be used in conjunction with the fifth through ninth embodiments, the score may be computed based on a variability in measurement of a spectrometry standard across a plurality of spectrometry apparatuses.

According to an eleventh embodiment, which may be used in isolation or in conjunction with any of the first through tenth embodiments, a computing device may receive a mass spectrum generated by a mass spectrometry apparatus applying an acquisition method that determines a number of dimensions of separation available in the mass spectrum. The computing device may define a putative product ion spectrum for the mass spectrum, and may access a repository that stores a composite product ion spectrum matching the putative product ion spectrum. For each of the dimensions of separation, the computing device may retrieve a regression curve generated based on the composite product ion spectrum, and may generate a normalized mass spectrum by applying respective regression curves to normalize a value of a corresponding dimension of separation.

According to a twelfth embodiment that may be used in conjunction with the eleventh embodiment, the respective regression curves may be applied to raw peak detections in the mass spectrum to correct for a variation in at least one of time, mass-to-charge ratio, or drift.

According to a thirteenth embodiment that may be used in conjunction with any of the eleventh through twelfth embodiments, the mass spectrum may be a first mass spectrum and the mass spectrometry apparatus may be a first mass spectrometry apparatus. The computing device may further receive a second mass spectrum generated by a second mass spectrometry apparatus different from the first mass spectrometry apparatus, normalize the second mass spectrum using the composite product ion spectrum, and validate that the second mass spectrum reproduces the first mass spectrum by comparing the normalized second mass spectrum to the first normalized mass spectrum.

According to a fourteenth embodiment that may be used in conjunction with any of the eleventh through thirteenth embodiments, the first mass spectrometry apparatus may be a different type of instrument platform than the first mass spectrometry apparatus.

According to a fifteenth embodiment that may be used in conjunction with any of the eleventh through fourteenth embodiments, the first mass spectrometry apparatus may be a different type of instrument platform than the first mass spectrometry apparatus.

According to a sixteenth embodiment that may be used in conjunction with any of the eleventh through fifteenth embodiments, the putative product ion spectrum may be clustered into ion clusters, and the computing device may re-cluster the putative product ion spectrum based on the normalized values.

According to a seventeenth embodiment that may be used in conjunction with the sixteenth embodiment, the putative production ion spectrum may be clustered by: calculating a theoretical isotope distribution for the putative product ion spectrum; clustering the putative product ion spectrum based on the theoretical isotope distribution; determining that an intensity of an isotope present in the mass spectrum exceeds a predetermined threshold amount; creating a virtual ion from an excess of the isotope; and clustering the virtual ion into a new isotope group.

According to an eighteenth embodiment that may be used in conjunction with any of the eleventh through seventeenth embodiments, the computing device may receive a list of two or more target molecules to be identified in a sample for which the mass spectrum was generated. The computing device may further select a target library customized to the sample, the target library comprising a set of precursor and product ions used to identify the two or more target molecules, wherein the target library consists of a subset of precursor and product ions represented in the mass spectrum. The computing device may use the target library to determine whether the target molecules are present in the sample.

According to a nineteenth embodiment that may be used in conjunction with any of the eleventh through eighteenth embodiments, the subset of precursor and product ions may be a minimal subset necessary to identify the target molecules in the mass spectrum.

According to a twentieth embodiment that may be used in conjunction with any of the eleventh through nineteenth embodiments, the normalized values for the dimensions of separation may each be associated with a match tolerance, the match tolerance defining a window over which the normalized mass spectrum will be considered to match a target spectrum.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
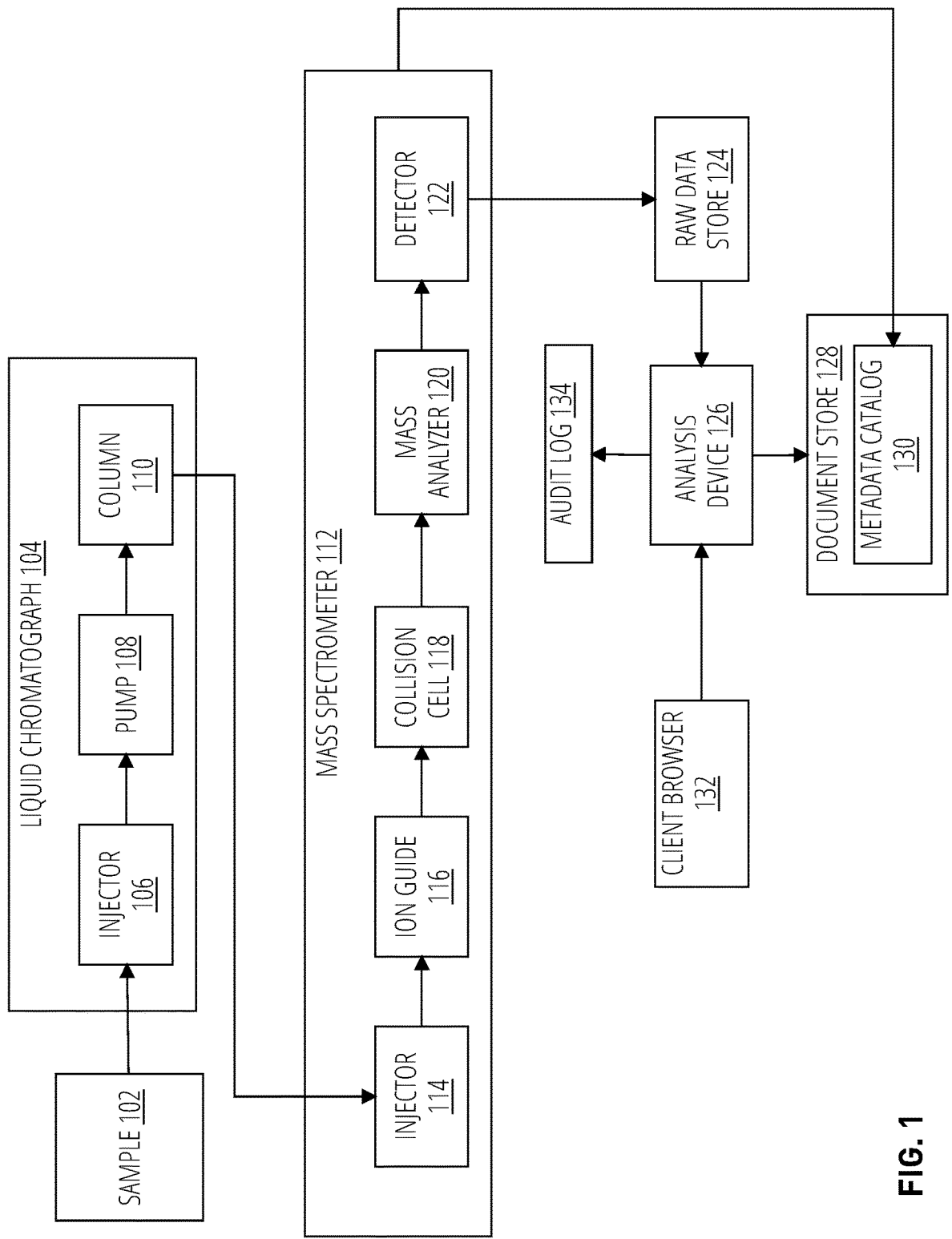
FIG. 1 illustrates an example of a mass spectrometry system according to an exemplary embodiment.

Conventionally, the life cycle of a cohort of liquid chromatography-mass spectrometry (LC-MS) experiments consists of processing, interpretation, and drawing conclusions, followed by storing information in an offline storage medium. Often, data processing software is restricted by sample type, instrument platform, and acquisition method. Comparing and contrasting similar data sets within and between laboratories, using different sample preparation methods, instrument platforms, acquisition methods and gradients, is challenging.

However, regardless of how the sample was prepared or what instrument platform and acquisition method was used, a molecule's mass and hydrophobicity are immutable characteristics. Furthermore, provided that the instruments used in the comparison employ a similar mechanism of fragmentation (e.g., collision cell) and are operated according to the manufacturer's instructions, a molecule's fragmentation pattern is very similar across instruments.

By leveraging these insights, exemplary embodiments provide methods, mediums, and systems capable of comparing spectrometry data acquired within and between cohorts from multiple laboratories and/or multiple experimental devices of different types; embodiments are agnostic as to sample type, instrument platform, and acquisition method. These embodiments can increase identification rates while reducing false discovery rates.

In order to achieve these improvements, exemplary embodiments may detects ions, create spectra, perform cross-sample and cross-cohort clustering, conduct spectral validation, search multiple databases, extract matched precursor and product ions, create offline and online putative libraries of both matched and unmatched spectra, validate identified spectra, and use the validated molecular ion spectra to screen normalized peak detections for all target compounds. Using the principles of successive approximation, iterative analysis, and the law of large numbers, exemplary embodiments transform data from multiple instrument platforms into a series of validated target molecular ion spectra.

As an aid to understanding, a series of examples will first be presented before detailed descriptions of the underlying implementations are described. It is noted that these examples are intended to be illustrative only and that the present invention is not limited to the embodiments shown.

Reference is now made to the drawings, wherein like reference numerals are used to refer to like elements throughout. In the following description, for purposes of explanation, numerous specific details are set forth in order to provide a thorough understanding thereof. However, the novel embodiments can be practiced without these specific details. In other instances, well known structures and devices are shown in block diagram form in order to facilitate a description thereof. The intention is to cover all modifications, equivalents, and alternatives consistent with the claimed subject matter.

In the Figures and the accompanying description, the designations "a" and "b" and "c" (and similar designators) are intended to be variables representing any positive integer. Thus, for example, if an implementation sets a value for a=5, then a complete set of components 122 illustrated as components 122-1 through 122-a may include components 122-1, 122-2, 122-3, 122-4, and 122-5. The embodiments are not limited in this context.

For purposes of illustration, FIG. 1 is a schematic diagram of a system that may be used in connection with techniques herein. Although FIG. 1 depicts particular types of devices in a specific LCMS configuration, one of ordinary skill in the art will understand that different types of chromatographic devices (e.g., MS, tandem MS, etc.) may also be used in connection with the present disclosure.

A sample 102 is injected into a liquid chromatograph 104 through an injector 106. A pump 108 pumps the sample through a column 110 to separate the mixture into component parts according to retention time through the column.

The output from the column is input to a mass spectrometer 112 for analysis. Initially, the sample is desolved and ionized by a desolvation/ionization device 114. Desolvation can be any technique for desolvation, including, for example, a heater, a gas, a heater in combination with a gas or other desolvation technique. Ionization can be by any ionization techniques, including for example, electrospray ionization (ESI), atmospheric pressure chemical ionization (APCI), matrix assisted laser desorption (MALDI) or other ionization technique. Ions resulting from the ionization are fed to a collision cell 118 by a voltage gradient being applied to an ion guide 116. Collision cell 118 can be used to pass the ions (low-energy) or to fragment the ions (high-energy).

Different techniques (including one described in U.S. Pat. No. 6,717,130, to Bateman et al., which is incorporated by reference herein) may be used in which an alternating voltage can be applied across the collision cell 118 to cause fragmentation. Spectra are collected for the precursors at low-energy (no collisions) and fragments at high-energy (results of collisions).

The output of collision cell 118 is input to a mass analyzer 120. Mass analyzer 120 can be any mass analyzer, including quadrupole, time-of-flight (TOF), ion trap, magnetic sector mass analyzers as well as combinations thereof. A detector 122 detects ions emanating from mass analyzer 122. Detector 122 can be integral with mass analyzer 120. For example, in the case of a TOF mass analyzer, detector 122 can be a microchannel plate detector that counts intensity of ions, i.e., counts numbers of ions impinging it.

A raw data store 124 may provide permanent storage for storing the ion counts for analysis. For example, raw data store 124 can be an internal or external computer data storage device such as a disk, flash-based storage, and the like. An analysis device 126 analyzes the stored data. Data can also be analyzed in real time without requiring storage in a storage medium 124. In real time analysis, detector 122 passes data to be analyzed directly to computer 126 without first storing it to permanent storage.

Collision cell 118 performs fragmentation of the precursor ions. Fragmentation can be used to determine the primary sequence of a peptide and subsequently lead to the identity of the originating protein. Collision cell 118 includes a gas such as helium, argon, nitrogen, air, or methane. When a charged precursor interacts with gas atoms, the resulting collisions can fragment the precursor by breaking it up into resulting fragment ions. Such fragmentation can be accomplished as using techniques described in Bateman by switching the voltage in a collision cell between a low voltage state (e.g., low energy, <5 V) which obtains MS spectra of the peptide precursor, with a high voltage state (e.g., high or elevated energy, >15V) which obtains MS spectra of the collisionally induced fragments of the precursors. High and low voltage may be referred to as high and low energy, since a high or low voltage respectively is used to impart kinetic energy to an ion.

Various protocols can be used to determine when and how to switch the voltage for such an MS/MS acquisition. For example, conventional methods trigger the voltage in either a targeted or data dependent mode (data-dependent analysis, DDA). These methods also include a coupled, gas-phase isolation (or pre-selection) of the targeted precursor. The low-energy spectra are obtained and examined by the software in real-time. When a desired mass reaches a specified intensity value in the low-energy spectrum, the voltage in the collision cell is switched to the high-energy state. The high-energy spectra are then obtained for the pre-selected precursor ion. These spectra contain fragments of the precursor peptide seen at low energy. After sufficient high-energy spectra are collected, the data acquisition reverts to low-energy in a continued search for precursor masses of suitable intensities for high-energy collisional analysis.

Different suitable methods may be used with a system as described herein to obtain ion information such as for precursor and product ions in connection with mass spectrometry for an analyzed sample. Although conventional switching techniques can be employed, embodiments may also use techniques described in Bateman which may be characterized as a fragmentation protocol in which the voltage is switched in a simple alternating cycle. This switching is done at a high enough frequency so that multiple high- and multiple low-energy spectra are contained within a single chromatographic peak. Unlike conventional switching protocols, the cycle is independent of the content of the data. Such switching techniques described in Bateman, provide for effectively simultaneous mass analysis of both precursor and product ions. In Bateman, using a high- and low-energy switching protocol may be applied as part of an LC/MS analysis of a single injection of a peptide mixture. In data acquired from the single injection or experimental run, the low-energy spectra contains ions primarily from unfragmented precursors, while the high-energy spectra contain ions primarily from fragmented precursors. For example, a portion of a precursor ion may be fragmented to form product ions, and the precursor and product ions are substantially simultaneously analyzed, either at the same time or, for example, in rapid succession through application of rapidly switching or alternating voltage to a collision cell of an MS module between a low voltage (e.g., generate primarily precursors) and a high or elevated voltage (e.g. generate primarily fragments) to regulate fragmentation. Operation of the MS in accordance with the foregoing techniques of Bateman by rapid succession of alternating between high (or elevated) and low energy may also be referred to herein as the Bateman technique and the high-low protocol.

The data acquired by the high-low protocol allows for the accurate determination of the retention times, mass-to-charge ratios, and intensities of all ions collected in both low- and high-energy modes. In general, different ions are seen in the two different modes, and the spectra acquired in each mode may then be further analyzed separately or in combination. The ions from a common precursor as seen in one or both modes will share the same retention times (and thus have substantially the same scan times) and peak shapes. The high-low protocol allows the meaningful comparison of different characteristics of the ions within a single mode and between modes. This comparison can then be used to group ions seen in both low-energy and high-energy spectra.

In summary, such as when operating the system using the Bateman technique, a sample 102 is injected into the LC/MS system. The LC/MS system produces two sets of spectra, a set of low-energy spectra and a set of high-energy spectra. The set of low-energy spectra contain primarily ions associated with precursors. The set of high-energy spectra contain primarily ions associated with fragments. These spectra are stored in a raw data store 124. After data acquisition, these spectra can be extracted from the raw data store 124 and displayed and processed by post-acquisition algorithms in the analysis device 126.

Metadata describing various parameters related to data acquisition may be generated alongside the raw data. This information may include a configuration of the liquid chromatograph 104 or mass spectrometer 112 (or other chromatography apparatus that acquires the data), which may define a data type. An identifier (e.g., a key) for a codec that is configured to decode the data may also be stored as part of the metadata and/or with the raw data. The metadata may be stored in a metadata catalog 130 in a document store 128.

The analysis device 126 may operate according to a workflow, providing visualizations of data to an analyst at each of the workflow steps and allowing the analyst to generate output data by performing processing specific to the workflow step. The workflow may be generated and retrieved via a client browser 132. As the analysis device 126 performs the steps of the workflow, it may read read raw data from a stream of data located in the raw data store 124. As the analysis device 126 performs the steps of the workflow, it may generate processed data that is stored in a metadata catalog 130 in a document store 128; alternatively or in addition, the processed data may be stored in a different location specified by a user of the analysis device 126. It may also generate audit records that may be stored in an audit log 134.

Figure 8:
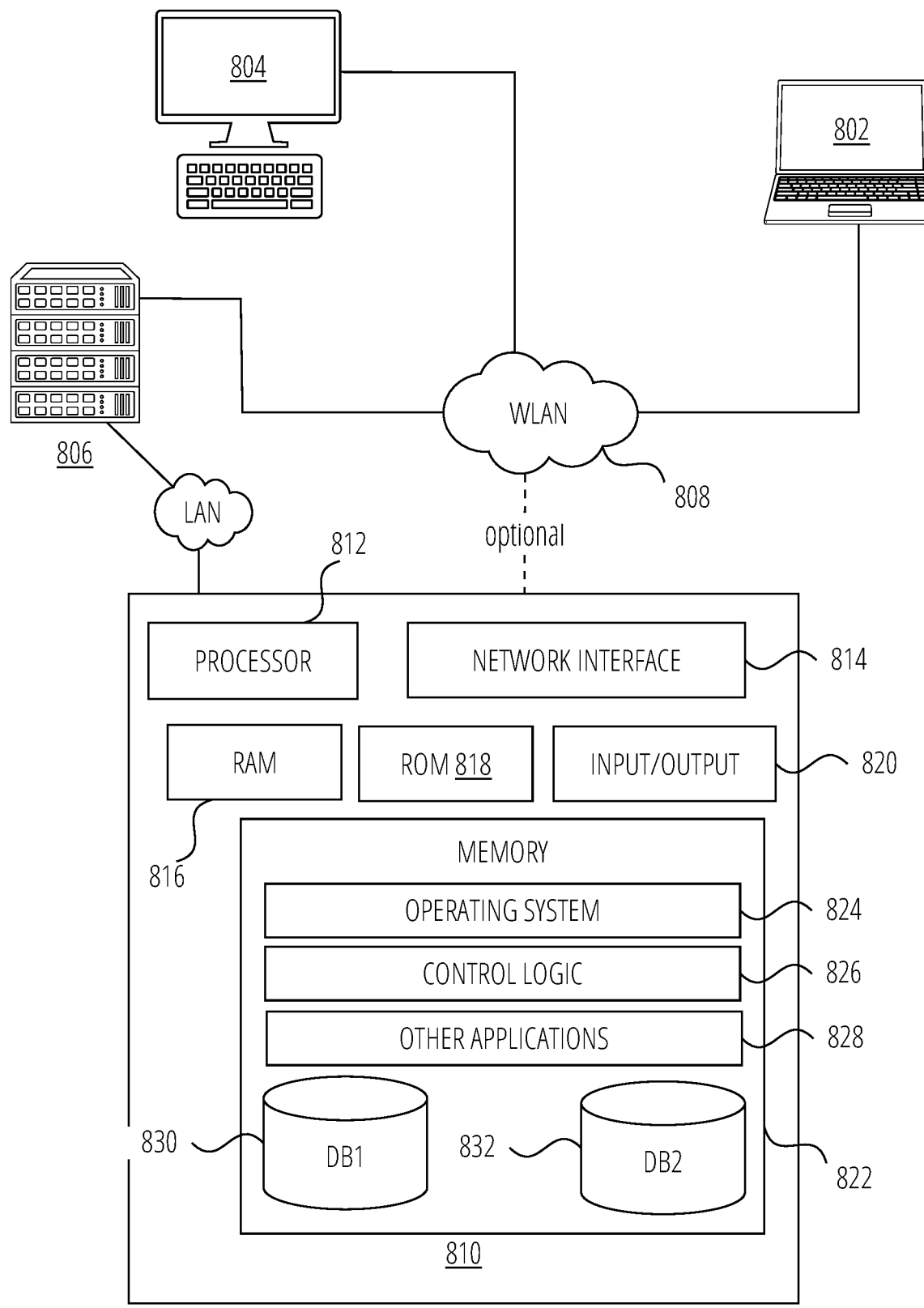
FIG. 8 depicts an illustrative computer system architecture that may be used to practice exemplary embodiments described herein.

The exemplary embodiments described herein may be performed at a number of locations, such as the client browser 132 and analysis device 126. An example of a device suitable for use as an analysis device 126 and/or client browser 132, as well as various data storage devices, is depicted in FIG. 8.

Figure 2:
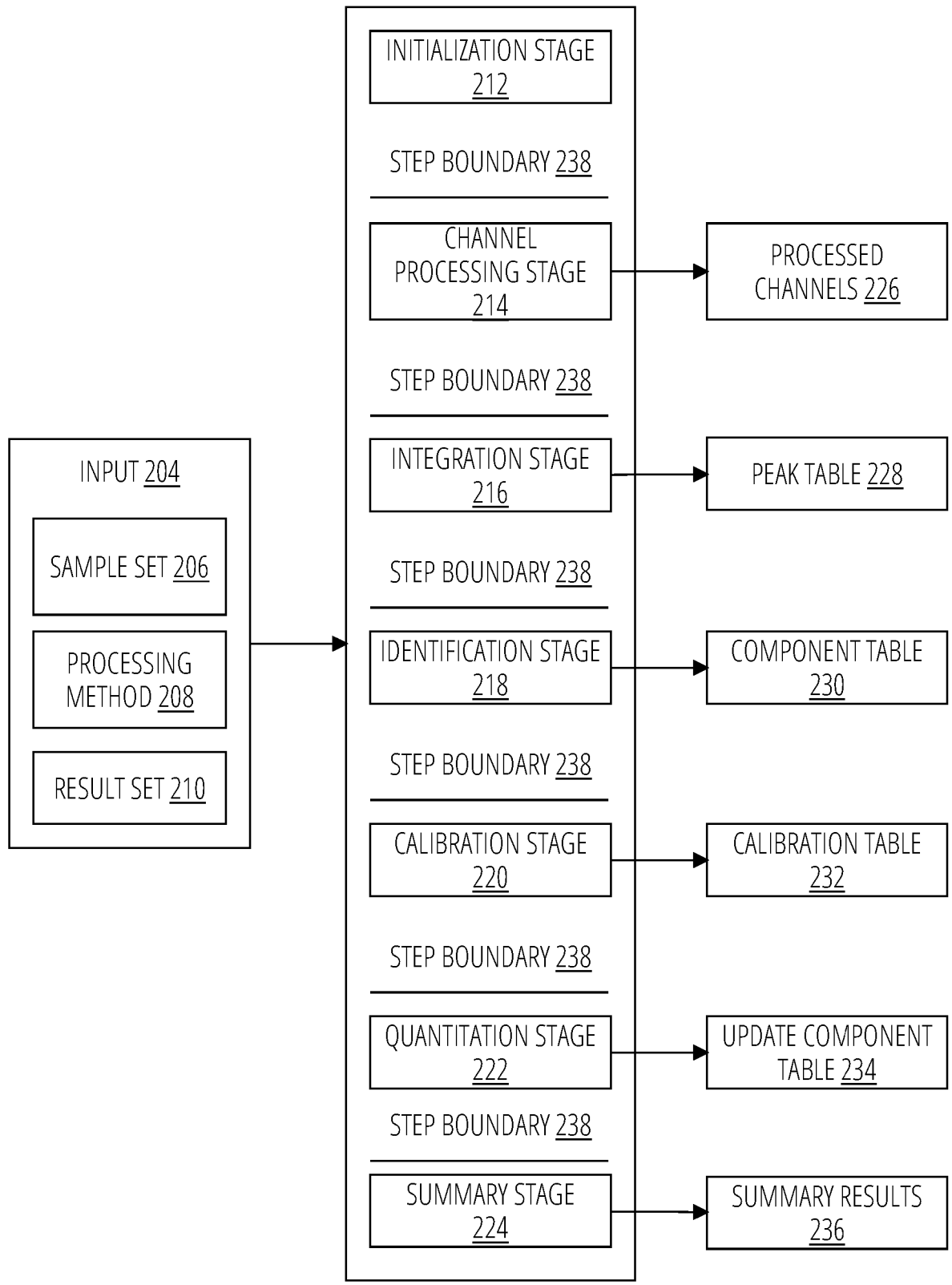
FIG. 2 illustrates an example of a workflow that operates on acquired data in accordance with one embodiment.

For context, FIG. 2 depicts a simplified example of a workflow 202 that may be applied by the analysis device 126 of FIG. 1. The workflow 202 is designed to take a set of inputs 204, apply a number of workflow steps or stages to the inputs to generate outputs at each stage, and continue to process the outputs at subsequent stages in order to generate results of the experiment. It is noted that the workflow 202 is a specific example of a workflow, and includes particular stages performed in a particular order. However, the present invention is not limited to the specific workflow depicted in FIG. 2. Other suitable workflows may have more, fewer, or different stages performed in different orders.

The initial set of inputs 204 may include a sample set 206, which includes the raw (unprocessed) data received from the chromatography experimental apparatus. This may include measurements or readings, such as mass-to-charge ratios. The measurements that are initially present in the sample set 206 may be measurements that have not been processed, for example to perform peak detection or other analysis techniques. The sample set 206 may include data in the form of a stream (e.g., a sequential list of data values received in a steady, continuous flow from an experimental apparatus).

In the context of the present application, the sample set 206 may represent the raw data stored in the raw data store 124 and returned by the endpoint interface. The sample set 206 may be represented as a model of a data stream (e.g., including data structures corresponding to data points gathered by the chromatography apparatus). The workflow 202 may be performed on the sample set 206 data by an application running on the analysis device 126 and/or running within a data ecosystem.

The initial set of inputs 204 may also include a processing method 208, which may be a template method (as discussed above) that is applied to (and hence embedded in) the workflow 202. The processing method 208 may include settings to be applied at various stages of the workflow 202.

The initial set of inputs 204 may also include a result set 210. When created, the result set 210 may include the information from the sample set 206. In some cases, the sample set 206 may be processed in some initial manner when copied into the result set 210—for example, MS data may require extracting, smoothing, etc. before being provided to a workflow 202. The processing applied to the initial result set 210 may be determined on a case-by-case basis based on the workflow 202 being used. Once the raw data is copied from a sample set 206 to create a result set 210, that result set 210 may be entirely independent from the sample set 206 for the remainder of its lifecycle.

The workflow 202 may be divided into a set of stages. Each stage may be associated with one or more stage processors that perform calculations related to that stage. Each stage processor may be associated with stage settings that affect how the processor generates output from a given input.

Stages may be separated from each other by step boundaries 238. The step boundaries 238 may represent points at which outputs have been generated by a stage and stored in the result set, at which point processing may proceed to the next stage. Some stage boundaries may require certain types of input in order to be crossed (for example, the data generated at a given stage might need to be reviewed by one or more reviewers, who need to provide their authorization in order to cross the step boundary 238 to the next stage). Step boundaries 238 may apply any time a user moves from one stage to a different stage, in any direction. For example, a step boundary 238 exists when a user moves from the initialization stage 212 to the channel processing stage 214, but also exists when a user attempts to move backwards from the quantitation stage 222 back to the integration stage 216. Step boundaries 238 may be ungated, meaning that once a user determines to move to the next stage no further input (or only a cursory input) is required, or gated, meaning that the user must provide some sort of confirmation indicating that they wish to proceed to a selected stage (perhaps in response to a warning raised by the analysis device 126), or a reason for moving to a stage, or credentials authorizing the workflow 202 to proceed to the selected stage.

In an initialization stage 212, each of the stage processors may respond by clearing the results that it generates. For example, the stage processor for the channel processing stage 214 may clear all its derived channels and peak tables (see below). At any point in time, clearing a stage setting may clear stage tracking from the current stage and any subsequent stage. In this example, the initialization stage 212 does not generate any output.

After crossing a step boundary 238, processing may proceed to a channel processing stage 214. As noted above, chromatography detectors may be associated with one or more channels on which data may be collected. At the channel processing stage 214, the analysis device 126 may derive a set of processing channels present in the data in the result set 210, and may output a list of processed channels 226. The list of processed channels 226 may be stored in a versioned sub-document associated with the channel processing stage 214, which may be included in the result set 210.

After crossing a step boundary 238, processing may proceed to an integration stage 216, which identifies peaks in the data in the result set 210 based on the list of processed channels 226. The integration stage 216 may identify the peaks using techniques specified in the settings for the integration stage 216, which may be defined in the processing method 208. The integration stage 216 may output a peak table 228 and store the peak table 228 in a versioned sub-document associated with the integration stage 216. The sub-document may be included in the result set 210.

After crossing a step boundary 238, processing may proceed to identification stage 218. In this stage, the analysis device 126 may identify components in the mixture analyzed by the chromatography apparatus based on the information in the peak table 228. The identification stage 218 may output a component table 230, which includes a list of components present in the mixture. The component table 230 may be stored in a versioned sub-document associated with the identification stage 218. The sub-document may be included in the result set 210.

After crossing a step boundary 238, processing may proceed to calibration stage 220. During a chromatography experiment, calibration compounds may be injected into the chromatography apparatus. This process allows an analyst to account for subtle changes in electronics, cleanliness of surfaces, ambient conditions in the lab, etc. throughout an experiment. In the calibration stage 220, data obtained with respect to these calibration compounds is analyzed and used to generate a calibration table 232, which allows the analysis device 126 to make corrections to the data to ensure that it is reliable and reproducible. The calibration table 232 may be stored in a versioned sub-document associated with the calibration stage 220. The sub-document may be included in the result set 210.

After crossing a step boundary 238, processing may proceed to quantitation stage 222. Quantitation refers to the process of determining a numerical value for the quantity of an analyte in a sample. The analysis device 126 may use the results from the previous stages in order to quantify the components included in the component table 230. The quantitation stage 222 may update 234 the component table 230 stored in the result set 210 with the results of quantitation. The updated component table 230 may be stored in a versioned sub-document associated with the quantitation stage 222. The sub-document may be included in the result set 210.

Included in each ion's metadata is the full width at half height for both mass and if ion mobility separation is employed. These half-heights are used to calculate mass and drift resolutions. These resolutions are then separated into m/z bins. For each bin a mean resolution is calculated as well as the standard deviation and coefficient of variations for each ion resident in that bin. This allows the ion detection algorithm to calculate each ions purity score. Basically, this process identifies interferences for de-convolution. This ensures high precision quantitative measurements. This technique ensues both highly accurate quantitative precursor ion areas as well as highly accurate normalized product ion spectra.

After crossing a step boundary 238, processing may proceed to summary stage 224. In the summary stage 224, the results of each of the previous stages may be analyzed and incorporated into a report of summary results 236. The summary results 236 may be stored in a versioned sub-document associated with the summary stage 224. The sub-document maybe included in the result set 210.

As used herein, a step may correspond to the above-noted stages. Alternatively, a single stage may include multiple steps, or multiple stages may be organized into a single step. In any event, all the activities performed in a given step should be performable by the same user or group of users, and each step is associated with one or more pages that describe a set of configuration options for the step (e.g., visualization options, review options, step configuration settings, etc.)

There may be a transition at some or all of the step boundaries 238, although not every step boundary 238 need be a transition. A transition may signify a change in responsibility for a set of data from a first user or group of users to a second, distinct user or group of users.

Overview of Molecular Ion Repository (MIR)

Mass spectrometers acquire and centroid ions over a preset acquisition time. Acquisition time is typically a function of chromatographic peak width. There is a balance between having enough scans across a peak to accurately determine its area and too many, which can adversely affect file size. Each scan contains three, or if ion mobility separation (IMS) is available, four numbers. These numbers refer to scan number, mass-to-charge ration (m/z), intensity, and drift time. Qualitative and quantitative results are derived from a series of algorithmic interpretations of these numbers, including peak detection, deisotoping, charge-state reduction, precursor and product ion alignment, database searching, and quantitation. In addition, there are algorithms that model isotope distributions and calculate peak widths (m/z, time, and drift) to correct for interferences.

Algorithms have an intrinsic degree of error referred to as the "95% rule". Here, error can be equated to a percent efficiency, assuming a "correct" result being 100%. For example, to illustrate the 95% rule, if two successive algorithms are applied to the data and each one produces results that are 95% correct, then the cumulative efficiency is: 0.95*0.95*100=90.25% correct. The more algorithms that are added to the sequence of processing steps, the greater the error and the lower the specificity. The serial application of multiple algorithms to the same data will reflect the cumulative errors. The more algorithms applied, the more inaccurate the results.

Sample complexity dictates the resolution requirements for available dimensions of separation required to successfully identify and quantify the largest number of compounds across the widest dynamic range. If the number of separation dimensions available and their respective resolving powers are not commensurate to sample complexity, interference will increase as will the combined algorithmic error, resulting in significantly compromised results. As an example, there are many isobaric lipids that separate chromatographically, provided the correct gradient. Gradient length has a profound effect on sample throughput. Increasing the gradient slope increases throughput to the detriment of isobaric separation. Isobaric lipids have the same m/z and if they are not chromatographically separated, the intensity reported is a composite. If IMS was available and the collisional cross section (CCS) of the two isoforms were unique and within the IMS resolving power, then increasing the gradient slope and, by extension sample throughput, would have little or no effect on the calculated intensity of each isoform. The added dimension of the IMS provides the means to increase throughput without compromising the ability to detect and accurately quantify isobaric species.

Interferences can be highly prevalent, but they can also be properly dealt with through repetition and verification across independent sample and/or data sets. Consider the case of tryptic peptides and lipids. The 20 naturally occurring amino acids are comprised of only six elements and are similarly distributed in all proteins. Lysine and Arginine, the preferred cleavage sites of trypsin, are both present at ~6%. If all amino acids were distributed equally, then enzymatic digestion with trypsin would, on average, result in a series of 10 residue peptides, each with a similar composition. Molecules of similar length and composition tend to have similar hydrophobicity. High concentration of molecular ions illustrating similar m/z and hydrophobicity lead to increased ion interferences because of coelution.

Exemplary embodiments create a list of identified chemical components with their relative intensities, precursor and products aligned across a set of samples. This is accomplished through continual refinement. Scan-by-scan spectra are correlated into sample-by-sample composites. The composites from each sample are then correlated into consensus spectra. These consensus spectra are used to create a library that is then used to screen the normalized peak lists.

The consensus is generated not from a single laboratory or single sample, but from multiple disparate data sets. Moreover, embodiments create target libraries not only on what is identified, but through continual refinement constructs consensus spectra on what is not identified.

In addition, measurement accuracy is a function of signal-to-noise. Selecting the apex scan as the reference allows exemplary embodiments to monitor an ion peak shape during elution. By monitoring the rate-of-change and scan-to-scan variability in m/z, the algorithm identifies interferences. It is highly unlikely that every ion will be interfered with in every scan in an LC-MS or LC-MS/MS analysis.

In Discovery mode (discussed in more detail below) exemplary embodiments may operate on as few as one unencumbered low-energy and high-energy scan to make an identification. There will always be some compromised product ion spectra; transitioning from product ion spectra to a consensus spectrum relies heavily on n (where n is an integer representing the number of samples). Following the law of large numbers, the average of the product ion spectra (Putative) obtained from a large number of samples should be close to the expected value (Composite) and will tend to become closer still (Consensus) as the number of cohorts increases. In practice, exemplary embodiments leverage replication for the removal of the false positives and for the aggregation of true positives into consensus spectra.

In some embodiments, a computing device may retrieve publicly available LC-MS and LC-MS/MS data from numerous laboratories, running different instrument platforms and acquisition methods. This data may be used to create and validate a molecular ion repository 318 (MIR; see FIG. 3). The MIR may be split into:
 a putatitive section 320
 a composite section 322
 a consensus section 324
 a target section 326

The putatitive section 320 contains all the matched and unmatched product ion spectra from each sample. The composite section 322 contains the correlated scan-by-scan spectra acquired on the same precursor ion during discovery. The consensus section 324 contains correlated composite spectra that have been reduced to only the most specific product ions or linked features (e.g., lipids in a class or pathway or peptides to a protein) for LC-MS datasets. The target section 326 section contains those minimum number of product ions required to correctly identify a consensus spectrum.

Figure 3:
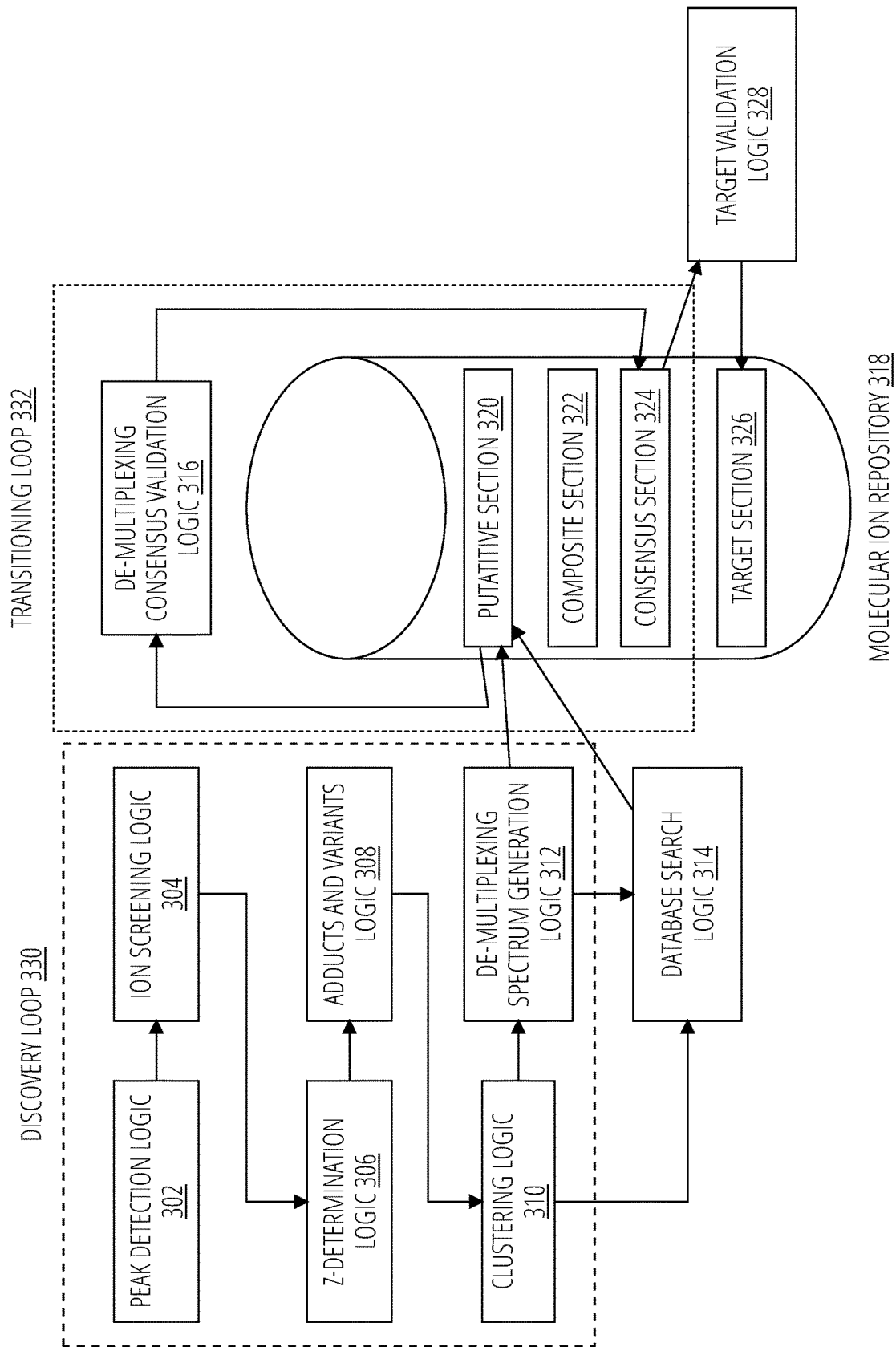
FIG. 3 illustrates a data flow diagram din accordance with one embodiment.

Molecules resident in the MIR may be grouped into:
 Peptides to proteins
 Proteins to pathways
 Lipids to classes
 Lipids to pathways
 Metabolites to pathways
 Metabolites to drugs A more detail explanation of the MIR and its operation is provided below in connection with FIG. 3. FIG. 3 depicts a data path through one exemplary embodiment in which MS data is subjected to validation using the exemplary MIR. The data path is divided into a discovery loop 330, an optional database search, a transitioning loop 332, and target validation. Note that these subdivisions are primarily organizational, and are described below with respect to various actions performed in each grouping (although other groupings may also be used in other embodiments).

The Discovery Loop

The following section describes an exemplary discovery loop 330 suitable for use with exemplary embodiments.

Peak detection logic 302 centers ion events scan-by-scan in all available dimensions of separation. The centering process determines the experimental m/z and drift resolutions.

Ion screening logic 304 may apply an ion screening filter (ISF) to bin raw peak detections according to the calculated m/z resolution. Each binned m/z value may be tracked across time. Peaks may be selected by: finding a local maximum; ensuring a minimal scan continuity over time in the neighborhood of the maximum; ensuring a minimal rate-of-change between scans within the neighborhood; and affirming that a minimum number of scans with centered intensities is at least equal to the mean of all neighboring scans.

Ions passing the ISF may be provided to z-determination logic 306, which performs charge determination and deisotoping. These ions may be sorted from low m/z to high m/z, the hypothesis being the lowest m/z of an isotope cluster is the $A_0$. Starting at the lowest m/z and using the same charge determination algorithm as previously described, each ion may be assigned a charge-state.

Once a charge has been assigned, an ion's molecular mass $(M_r)$ may be calculated by adducts and variants logic 308. Some molecules can support multiple charge states, with multiple adducts supporting each charge. Precursors illustrating the same $M_r$ may be grouped into a component group with the most intense member of the group labeled as the principal.

Once the ions have been assembled into isotope groups, clustering logic 310 may apply an averagine (the average elemental composition of all amino acids) as the isotope model. The clustering logic 310 may calculate and compare the calculated theoretical isotope distribution to the experimental. If the experimental intensity of any isotope in an isotope group exceeds 125% of the theoretical, the algorithm may create a "virtual" ion from the excess. The process repeats until all virtual ions are clustered into new isotope groups or are abandoned.

Once a peak has been validated and all the related charge-states and adducts are assembled into a component group, the product ions illustrating the same metadata may be paired, scan-by-scan, to their respective precursor. The clustering logic 310 may conclude with a product ion spectrum for each precursor ion cluster in each scan. A normalized area intensity ratio ($AR_3$) may be calculated for each aligned product ion to a precursor:

$AR_3$=Product Ion Intensity/S Product Ion Intensity

At the conclusion of the clustering logic 310, the single-scan product ion spectra can either be directly deposited into the putative section 320 of molecular ion repository 318, sent to de-multiplexing spectrum generation logic 312, or directly sent to a database search engine to apply database search logic 314.

Optional Composite Generation and Database Searching

Composite product ion spectra may be generated using de-multiplexing spectrum generation logic 312 by summing the product ion spectra across the peak. Only those product ions present in a minimum of n/2+1 scans illustrating a similar rate-of-change as the precursor may be retained as a composite ion, where n is an integer representing the total number of scans. Similarly, a normalized intensity ratio $AR_3$ may be calculated for each product ion passing a minimum match criteria. A standard error may be calculated on all single scan product ion $AR_3$ values across the peak. The de-multiplexing spectrum generation logic 312 may also calculates a standard error on the scan-by-scan isotope distributions of both the precursor and product ions making up the composite spectra. These statistics provide the means for the algorithm to identify interferences. Product ions with coefficients of variation less than 30% may be retained for either deposition into the putatitive section 320 of the molecular ion repository 318 or, if searchable, sent to a database search engine.

In samples where optional database searching is performed, database search logic 314 may retain all matched ions and calculate new $AR_3$ ratios. The matched spectra are then deposited into the putatitive section 320 of the molecular ion repository 318. In data acquisition independent (DIA) acquisitions, product ions are typically shared with more than one precursor. To that end, matched product ions are removed from the unmatched spectra and new $AR_3$ ratios are calculated using the remaining product ions. The unmatched spectra are then uploaded into the putatitive section 320 of the molecular ion repository 318, where they are clustered and then re-searched with the process continuing until no new identifications are made. Removal of the matched product ions may increase the accuracy of each $AR_3$ value.

Transitioning Loop

The transitioning loop 332 applies de-multiplexing consensus validation logic 316 to continually query the putatitive section 320 of the molecular ion repository 318 for product ion spectra exhibiting a minimum match count meeting or exceeding a predetermined threshold value m (e.g., 50). Spectra exceeding the minimum count may be extracted (block 402 of FIG. 4) and their fragment patterns may be correlated by m/z. $AR_3$ ratio, and drift, if IMS is employed (block 404 of FIG. 4). After the initial correlation, standard errors may be calculated on all matched product ion m/z values, $AR_3$ ratios, retention, and drift times (block 406 of FIG. 4). A composite spectrum is generated if the product ion match count meets or exceeds a predetermined threshold value (e.g., 38) and the $AR_3$ standard errors are at or below a predetermined value (e.g., 0.35) (block 408 of FIG. 4). The metadata associated with each transitioning composite spectrum includes: the theoretical m/z values for both precursor and products (for targeting); the mean $AR_3$ ratios of each product ion; the mean retention time; the mean drift time, if IMS is available; the coefficient of variation for each product ion; and a mean product ion intensity.

Figure 4:
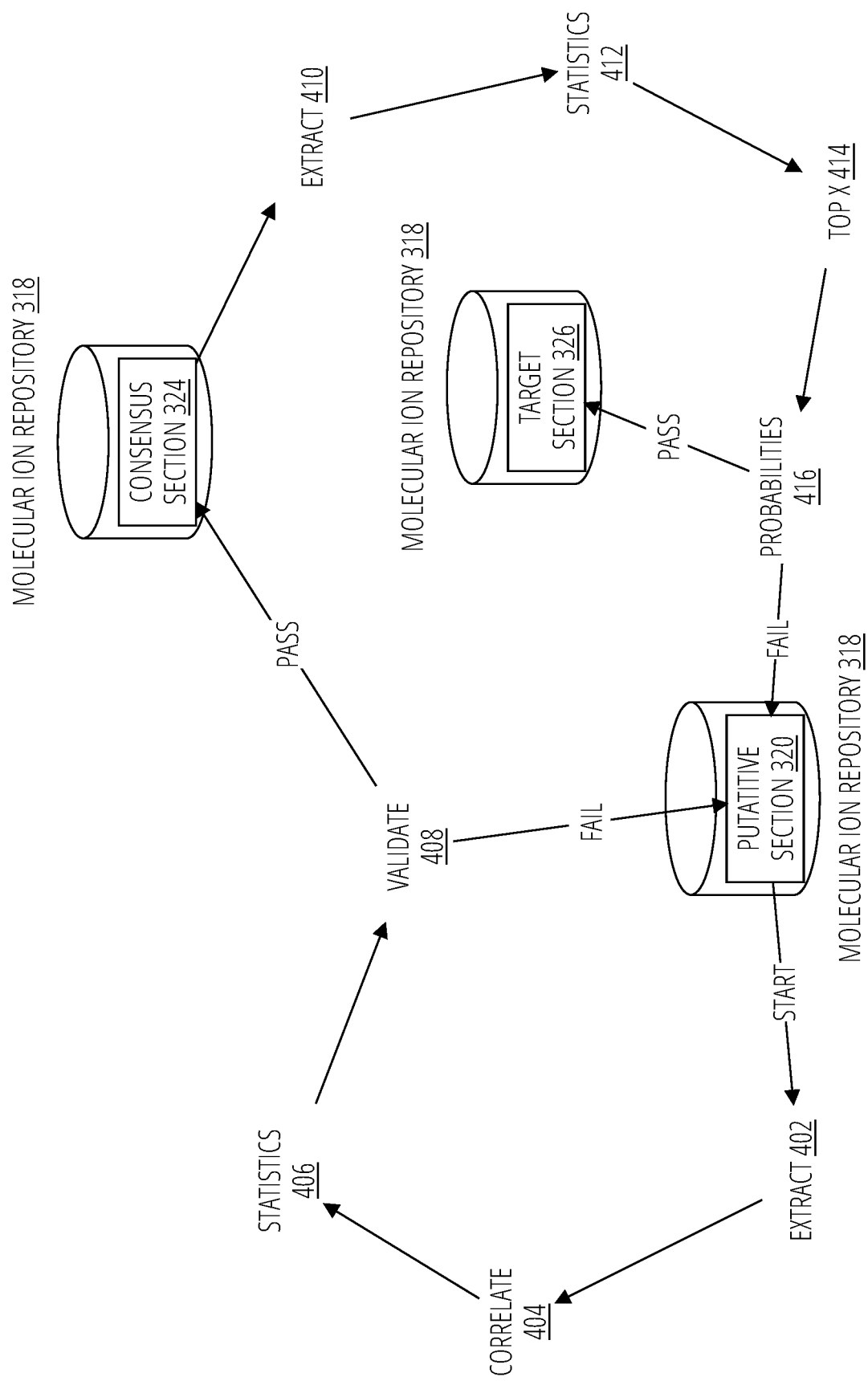
FIG. 4 illustrates an exemplary target discovery and validation environment in accordance with one embodiment.

Extracted spectra that failed to transition are redeposited for a future pass ("fail" at block 408 of FIG. 4). When the match rate of an initially failed set of putative spectra increases by 20%, a trigger event causes a different random set of m product ion spectra to be extracted and the process repeats. The transition loop is continuous, cycling each time the putative section of the MIR is refreshed. Refreshment can be hourly, daily, weekly, or monthly depending on processing rate. Molecular attributes such as hydrophobicity index, isoelectric point, and elemental composition may be extracted and utilized to update the retention time and CCS prediction algorithms.

Once a minimum number (i.e., above a predefined minimum threshold value) of composite spectra are retained ("pass" at block 408 of FIG. 4), the de-multiplexing consensus validation logic 316 may extract the composite spectra from the composite section 322 (block 410 of FIG. 4). The composite spectra may be correlated to reduce the number of product ions to only those that are most specific to that molecule. Those that pass transition from the composite section 322 to the consensus section 324 of the molecular ion repository 318.

The Molecular Ion Repository (MIR)

There are five distinct groups of product ion spectra and LC/MS features residing in the molecular ion repository 318:

putative (initial scan-by-scan aligned spectra),
putative (correlated scan-by-scan spectra),
composite (correlated putative spectra from across a sample),
consensus (correlated composites across the cohort), and
target (a minimal highly selective consensus spectra).

At the end of the discovery loop 330, single scan and composite product ion spectra have two routes forward: first, into the putatitive section 320 of the molecular ion repository 318 and subsequently directly into the database search engine. For LC/MS processing all features may be directly transferred to the molecular ion repository 318. In place of a product ion spectra a pseudo spectrum is made of all the ions in that scan. Provided the column matrix and buffer compositions are similar, elution order maybe retained creating a linked set of features akin to a putative product ion spectrum. These linked features are then treated similarly to the previously described MS/MS spectra. While residing in the molecular ion repository 318 the putative product ion spectra or LC/MS features for each sample are ordered by intensity. In proteomics samples identified peptides may be grouped into proteins and ranked in descending order by intensity. Peptide intensities may then be summed, and the identified proteins may be ranked, descending by intensity. A similar grouping and ranking process may be applied to small molecules. Whereas peptides are grouped into proteins, lipids are group by class or a pathway, with metabolites grouped by pathway or drug. Thus, regardless of sample type, the molecular ion repository 318 contains the intensity rank order of all putative product ion spectra or LC/MS features per sample.

Discovery Normalization

The composite product ion spectra or LC/MS features generated from each cohort may be matched to each individual sample's putative product ion spectra or LC/MS features from that cohort. Once matched, discovery normalization logic may generate regression curves for each of the available dimensions of separation. Each regression may be applied to the ion screened raw ion detections. The normalized m/z, retention and drift times may be used to re-cluster the putative product ion spectra or LC/MS features across the cohort. The discovery normalization logic also calculates the match tolerances for each dimension of separation across the cohort for the subsequent targeting loop.

Target Validation

The target validation logic 328 continually queries the consensus section 324 of the molecular ion repository 318 for new consensus spectra. The target validation logic 328 performs a correlation analysis comparing the normalized product ion intensities of the matched product ions. The same correlation analysis is performed on linked features in LCMS data. All composite product ion spectra and linked features illustrating a correlation coefficient >0.7 are retained and provided a passed count rate of >n/2+1 an initial consensus spectra or linked feature list is generated and store in the MIR The number of target product ions may be determined by the following precursor attributes:

Molecular Mass $M_r$,
rank intensity, and
charge z.

The criteria for product ion selection includes:

Match rate,
Intensity
Frequency and
AR3 variation

Each of the four selection criteria may be assigned a score (block 412 in FIG. 4):

Match Rate/Max Match Rate Over the Feature ID,
Intensity/Max Intensity Over the Feature ID, and
Frequency—the number of times a product ion is found in the consensus library.

The four scores are multiplied, and the product ions are ranked in descending order by score (block 414 of FIG. 4). The number of product ions that can be validated is a function of the molecule's mass, intensity, and disassociation kinetics. Small molecules generally are singly charged and have lower $M_r$. In addition, the fragmentation kinetics are such that many product ions are much lower in intensity than the primary fragment. The number of product ions that can be validated is primarily a function of the precursor ion intensity. For example, with respect to tryptic peptides the number of target product ions may be a minimum (e.g.) of 5 up to a maximum (e.g.) of 10. As the resolution and/or number of dimensions of separation increase, each product ion's frequency decreases while its score increases, making frequency the predominate factor in product ion selection. In contrast, as the number of dimensions and/or resolution decrease, the match rate, intensity, and the number of linked features have greater influence.

Each frequency count may be transformed into a probability score (block 416 of FIG. 4). The probability score reflects the chance of finding each target ion as a random event (e.g., a probability of misidentifying the target ion). Multiplication of the probabilities provides the likelihood of finding all target ions and the precursor as a random event. This likelihood may be translated into a PPM FDR, and if the FDR is less than a predetermined threshold ("pass" at block 416 in FIG. 4), the target product ions under analysis may be selected for the cohort.

Once the target product ions have been selected for a cohort, the target spectra may be transitioned to the target section 326 of the molecular ion repository 318. Target selection is dynamic in that it automatically adjusts to changes in sample complexity, resolution, and/or the number of dimensions of separation available to the cohort(s) being analyzed. The process culminates in a target list comprised of the most reproducible, lowest frequency, lowest probability product ions or linked features for each consensus product ion spectrum resident in the molecular ion repository 318.

The path to a target product ion spectra or group of linked features (pathways, classes, protein) is illustrated in FIG. 4 and has already been described in detail above. In brief summary, the continual refinement loops of exemplary embodiments culminate in a target library uniquely selected for that sample. The target library contains the minimal number of product ions and/or linked features necessary to identify all the target compounds resident to the library in any sample, cohort, or series of cohorts with an exceedingly low FDR rate.

Figure 5:
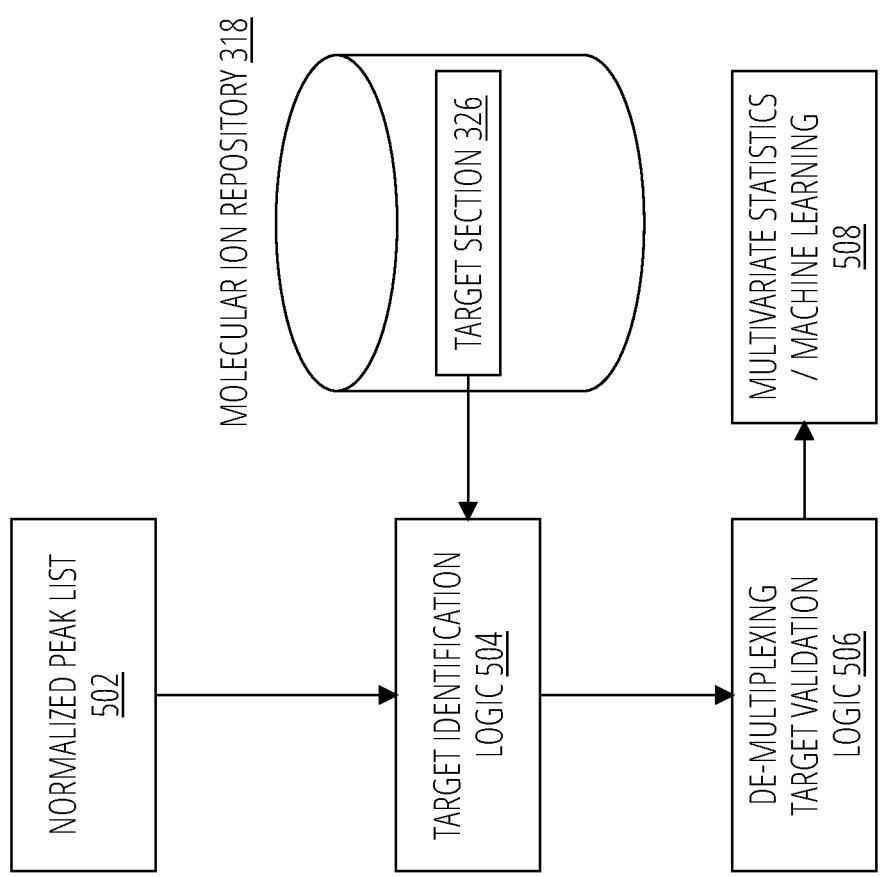
FIG. 5 illustrates an exemplary target validation environment in accordance with one embodiment.

FIG. 5 illustrates how the target section 326 of the molecular ion repository 318 may be applied to incoming data in a targeting loop.

After the data is collected, a normalized peak list 502 may be generated through post discovery normalization. A number of target ions uniquely selected for the applied number of separation dimensions and resolutions in the experiment may be input into target identification logic 504 along with the normalized peak list 502. The matched normalized peak detections may be clustered and scored by scan. For example, the normalized and target ions may be assembled into a series of independent grids or cubes. The method of isolation used is a function of the acquisition method and the number of dimensions of separation available. The width in time, drift, and m/z of each side of the grid or cube is determined by the discovery normalization logic.

When the paired grids or cubes are matched, the target ions must match not only to a single scan but a series of scans defining an eluting component. The number of contiguous matched scans must also be commensurate to the intensity of the apex scan. More complex or lower resolution samples may require more dimensions like $AR_3$, linked features, and additional product ions. The number of dimensions necessary to ensure a highly accurate result is a direct consequence of the required depth of coverage and the resolution of each available dimension of separation. As the number of dimensions and/or resolution increase, the probability of a target identification being identified incorrectly or as a random event decrease. The targeting loop calculates the frequency of m/z values in each grid or cube for both the precursor and product ions. Multiplying the calculated probabilities (frequency/count) of the target precursor ion and product ion m/z values (+/−10 ppm) in the raw data provides for two comparative probability measurements for finding all six ions in the exact same scan. The two comparative probabilities are from the grouped normalized peak detections and the consensus library. The specificity can be increased further by using retention time and/or drift time (CCS} tolerances to bound the frequency count of each m/z value. Thus, the probability of aligning these ions randomly is a function of m/z, retention-time, and drift time.

With proteomics, once a target peptide has been identified, the targeting algorithm generates all other possible product ion m/z values and screens them against the matching scans. Additional product ion matches increase selectivity by allowing the targeting algorithm to remove them from the normalized peak detections. As previously mentioned, mass analyzers measure isotopic distributions very well. Knowing each molecule's elemental composition and A intensity, allows the targeting algorithm to correct for any interference. The fitted area intensity of each isotopes of the precursor and product ions is removed. The remaining intensity is used to create virtual ions and together with the unmatched peak detections go through a second round of clustering. The newly generated spectra are researched through the same discovery loops as before terminating when no new identifications are found.

As illustrated with other putative identifications, the target identifications may be validated by de-multiplexing target validation logic 506 by correlating them using the above-described transitioning loop 332 to ensure reproducibility across all the samples in the cohort. The validated target identifications may then be grouped as previously described and transferred for analysis by multivariate statistics/machine learning 508.

Figure 6:
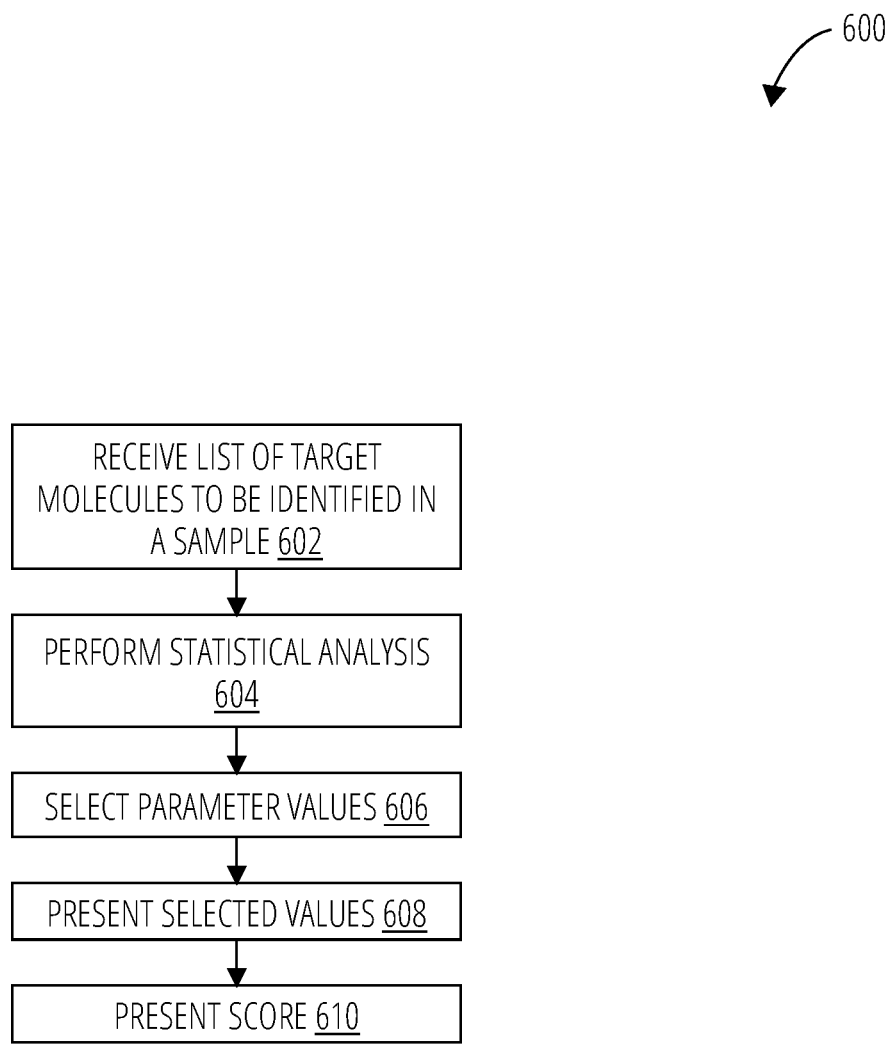
FIG. 6 is a flowchart depicting exemplary value selection logic 600 in accordance with one embodiment.

After the MIR and target library have been generated as discussed above, they can be used for a variety of purposes, such as validating whether mass spectra generated by different apparatuses, different users, different laboratories, etc. replicate each other, normalizing data for future comparison, determining whether target molecules are present in a sample, and other applications. FIG. 6 is a flow chart depicting exemplary logic for one such application: designing experiments to maximize the chances of finding target molecules (if they exist in a sample). For example, given a particular combination of target molecules, the logic may output an indication that an apparatus should be configured with an X-minute gradient at Y psi and a Z PPM mass accuracy.

Among other possibilities, the logical blocks of FIG. 6 may be implemented as instructions stored on a non-transitory computer-readable medium, a method performed by a computing device, or as a computing device programmed with instructions to perform the actions described.

At block 602, a computing device may receive, via a user interface, a list of two or more target molecules to be identified in a sample for analysis by a mass spectrometry apparatus according to an experimental method defined by a plurality of parameters. For example, the parameters may include a gradient slope, a pressure value, and/or a mass accuracy for an experimental apparatus.

At block 604, the device may perform a statistical analysis based on the list of two or more target molecules, the statistical analysis configured to determine a probability of misidentifying one or more of the target molecules in the list.

The statistical analysis may be based on data gathered by running a known standard multiple times on different machines, as stored in the MIR. Because different machines will inherently have some variances, the retention times between the different machines will likely differ.

Accordingly, a series of spectra can be retrieved from each machine, where the spectra include precursor (LCMS and LCMSMS) and product ions (LCMSMS). The ion detections may be sorted by intensity, so that across n samples, the most intense ion detections should be at the top of each sample. The n most-intense detections may then be sorted ascending by mass. Optionally, the masses may be binned (e.g., at 10 ppm).

The computing device determines how many times each mass is found across the cohort of samples. The goal is to assemble the data into groups of n, which would indicate that the ion detections occur once per sample and can therefore be aligned to each other.

If the number of times is greater than n (the number of samples), this means that the mass is present in the data at different retention times. The computing device may sort the ion detections by binned mass and then retention time. The retention times may also be binned (e.g., within 1 minute, 5 minutes, etc.).

If, when sorted by mass and time, the ion detections are in groups of n, then the detections occur once per sample and can therefore be aligned. For example, if n=15 and 15 detections of a given mass occur at 5 minutes, 15 occur at 10 minutes, and 15 occur at 15 minutes, the detections occur once per sample and can be aligned.

At each step, it can be determined if the data is aligned based on the current set of dimensions (mass, time, drift, etc.). If the number of detections cannot be arranged into groups of n at a given step, another dimension may be added and the detections may be sorted based on the new dimension.

After the ion detections are arranged into groups of n, the variance in time of each of the detections can be plotted (since the same molecule is supposed to occur in the data at the same point in time). The variability in drift times can be accounted for by mapping the differences on a regression line and aligning them. By measuring the change in normalized time, the variability can be measured. The variability then can be used to define the match tolerance. The tolerances afforded to each of the dimensions can be determined because the original sample was a standard, so the experimenter knows the makeup of the sample. For example, if the samples can be matched within X ppm, Y minutes, and Z drift bins, these values may define the parameters of the experimental apparatus needed to detect the identified target molecules with a high degree of accuracy.

In some embodiments, the statistical analysis may be performed based on a subset of target molecules in the list, the subset representing a group of relatively less common markers from among the target molecules. Because many molecules include a large number of common markers, finding these common markers may not provide much information about the molecules in the sample (since many different molecules could generate the common markers). By selecting the subset of target molecules based on which markers are relatively less common, a more accurate identification can be made more quickly.

At block 606, the device may select a set of values for the plurality of parameters that reduces the probability below a predetermined threshold value, and may present, on the user interface, the selected set of values.

In some embodiments, the values for the plurality of parameters may be selected based on a known multi-dimensional positioning of one or more of the target molecules and/or a known relationship between target molecules.

At block 608, the computing device may present, on the user interface, a score representing a likelihood that a presence or absence of the two or more target molecules will be correctly identified in the sample given the selected set of values.

Based on the above-noted variance, the computing device may determine, for a given parameter set, how likely it is that the target molecules will be identified given those parameters. This likelihood can be normalized and translated into the above-noted score.

In some embodiments, the score may be computed by: (a) consulting a consensus library comprising immutable attributes of spectral features; (b) counting a frequency at which one of the target molecules is present in the consensus library; (c) transforming the frequency count into a probability score; repeating steps (a)-(c) for a plurality of the target molecules; and multiplying the probability scores for the plurality of target molecules together. The score may be configured to increase as a function of a number of dimensions of separation available as determined by an acquisition method applied, and/or as a function of a resolving power of the all available separation systems employed. The score may be computed based on a combination of the two or more target molecules' mass-to-charge ratio, retention time, and drift time and/or based on a variability in measurement of a spectrometry standard across a plurality of spectrometry apparatuses. In other words, the score reflects how often a given mass is reflected with a given normalized time and drift, which is then translated into a probability. Combining the probabilities across all the molecules of interest limits the likelihood that the identified features would be detected by chance or as a random event.

Figure 7:
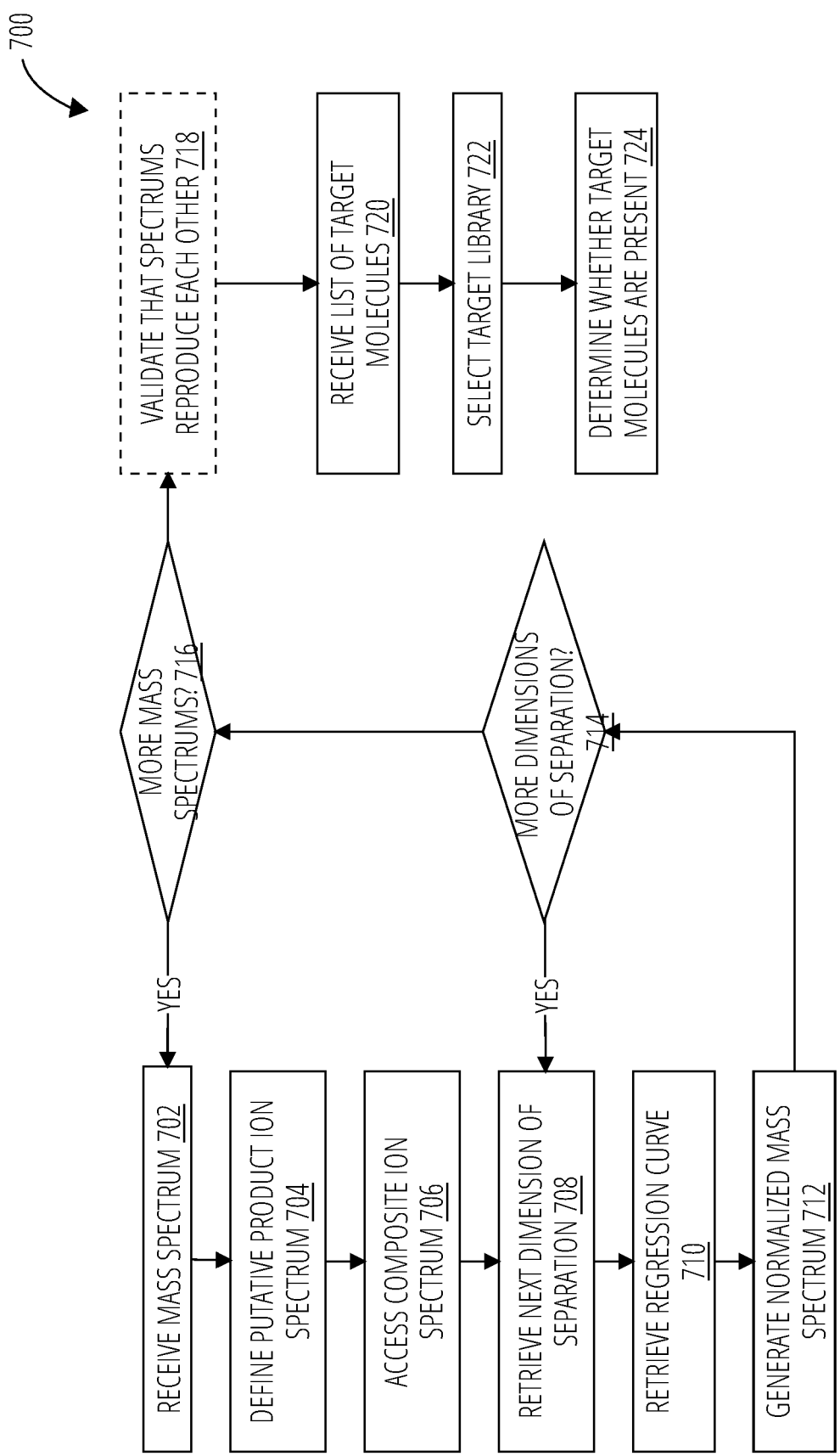
FIG. 7 is a flowchart depicting exemplary spectrum normalization and validation logic 700 in accordance with one embodiment.

FIG. 7 is a flow chart depicting exemplary logic for another application of the above-described MIR, normalizing acquired data for a variety of purposes.

Among other possibilities, the logical blocks of FIG. 7 may be implemented as instructions stored on a non-transitory computer-readable medium, a method performed by a computing device, or as a computing device programmed with instructions to perform the actions described.

At block 702, a computing device may receive a mass spectrum generated by a mass spectrometry apparatus applying an acquisition method that determines a number of dimensions of separation available in the mass spectrum.

At block 704, the computing device may define a putative product ion spectrum for the mass spectrum, using techniques similar to those discussed above in connection with generating the putative section of the MIR.

At block 706, the computing device may access a repository that stores a composite product ion spectrum matching the putative product ion spectrum. An example of such a repository is the above-described MIR.

At block 708, the computing device may retrieve the next dimension of separation to be considered. For each of the dimensions of separation, the computing device may (at block 710) retrieve a regression curve generated based on the composite product ion spectrum, and may (at block 712) generate a normalized mass spectrum by applying respective regression curves to normalize a value of a corresponding dimension of separation. The regression curves have been described above in connection with the Discovery Normalization process in FIG. 3. The respective regression curves may be applied to raw peak detections in the mass spectrum to correct for a variation in at least one of time, mass-to-charge ratio, or drift.

As noted above, normalizing a spectrum may involve clustering the putative product ion spectrum into ion clusters, and then re-clustering the putative product ion spectrum based on the normalized values. The clustering may be performed by: calculating a theoretical isotope distribution for the putative product ion spectrum; clustering the putative product ion spectrum based on the theoretical isotope distribution; determining that an intensity of an isotope present in the mass spectrum exceeds a predetermined threshold amount; creating a virtual ion from an excess of the isotope; and clustering the virtual ion into a new isotope group.

At block 714, the system determines whether more dimensions of separation remain to be considered. If so, processing reverts to block 708 and the next dimension of separation is retrieved. Otherwise, processing proceeds to decision block 716.

In some embodiments, the computing device may retrieve multiple mass spectrums and may validate them to determine whether the mass spectrums reproduce each other. To that end, at decision block 716 the device may determine if more spectrums remain to be analyzed. If so, processing reverts to block 702 and the next spectrum is selected and normalized, as described above.

After all spectrums have been analyzed ("no" at block 716), processing may proceed to block 718, where the device may validate that the spectrums reproduce each other. In order to do this, the normalized spectrums as created at each iteration of block 712 may be compared; because the spectrums have been normalized using the techniques described herein, the spectrums should now be directly comparable (e.g., within a predefined acceptable tolerance). To that end, the normalized values for the dimensions of separation may each be associated with a match tolerance (as discussed above in connection with FIG. 6), the match tolerance defining a window over which the normalized mass spectrum will be considered to match a target spectrum. This allows spectrums generated by different mass spectrometry apparatuses of different types (e.g., different platforms employing different acquisition methods) to be compared to each other.

In some embodiments, the computing device may further determine if a set of target molecules are present in the sample that generated the mass spectrum. To that end, at block 720, the computing device may receive a list of two or more target molecules to be identified in a sample for which the mass spectrum was generated. At block 722, the computing device may select a target library customized to the sample, the target library comprising a set of precursor and product ions used to identify the two or more target molecules, wherein the target library consists of a subset of precursor and product ions represented in the mass spectrum. In some embodiments, the subset of precursor and product ions may be a minimal subset necessary to identify the target molecules in the mass spectrum. The target library may be generated for the MIR according to the techniques described above. At block 724, the computing device may use the target library to determine whether the target molecules are present in the sample (using the "targeting" techniques described above), and may output an indication of the molecules' presence on a user interface.

FIG. 8 illustrates one example of a system architecture and data processing device that may be used to implement one or more illustrative aspects described herein in a stand-alone and/or networked environment. Various network nodes, such as the data server 810, web server 806, computer 804, and laptop 802 may be interconnected via a wide area network 808 (WAN), such as the internet. Other networks may also or alternatively be used, including private intranets, corporate networks, LANs, metropolitan area networks (MANs) wireless networks, personal networks (PANs), and the like. Network 808 is for illustration purposes and may be replaced with fewer or additional computer networks. A local area network (LAN) may have one or more of any known LAN topology and may use one or more of a variety of different protocols, such as ethernet. Devices data server 810, web server 806, computer 804, laptop 802 and other devices (not shown) may be connected to one or more of the networks via twisted pair wires, coaxial cable, fiber optics, radio waves or other communication media.

Computer software, hardware, and networks may be utilized in a variety of different system environments, including standalone, networked, remote-access (aka, remote desktop), virtualized, and/or cloud-based environments, among others.

The term "network" as used herein and depicted in the drawings refers not only to systems in which remote storage devices are coupled together via one or more communication paths, but also to stand-alone devices that may be coupled, from time to time, to such systems that have storage capability. Consequently, the term "network" includes not only a "physical network" but also a "content network," which is comprised of the data—attributable to a single entity—which resides across all physical networks.

The components may include data server 810, web server 806, and client computer 804, laptop 802. Data server 810 provides overall access, control and administration of databases and control software for performing one or more illustrative aspects described herein. Data serverdata server 810 may be connected to web server 806 through which users interact with and obtain data as requested. Alternatively, data server 810 may act as a web server itself and be directly connected to the internet. Data server 810 may be connected to web server 806 through the network 808 (e.g., the internet), via direct or indirect connection, or via some other network. Users may interact with the data server 810 using remote computer 804, laptop 802. e.g., using a web browser to connect to the data server 810 via one or more externally exposed web sites hosted by web server 806. Client computer 804, laptop 802 may be used in concert with data server 810 to access data stored therein, or may be used for other purposes. For example, from client computer 804, a user may access web server 806 using an internet browser, as is known in the art, or by executing a software application that communicates with web server 806 and/or data server 810 over a computer network (such as the internet).

Servers and applications may be combined on the same physical machines, and retain separate virtual or logical addresses, or may reside on separate physical machines. FIG. 8 illustrates just one example of a network architecture that may be used, and those of skill in the art will appreciate that the specific network architecture and data processing devices used may vary, and are secondary to the functionality that they provide, as further described herein. For example, services provided by web server 806 and data server 810 may be combined on a single server.

Each component data server 810, web server 806, computer 804, laptop 802 may be any type of known computer, server, or data processing device. Data server 810, e.g., may include a processor 812 controlling overall operation of the data server 810. Data server 810 may further include RAM 816, ROM 818, network interface 814, input/output interfaces 820 (e.g., keyboard, mouse, display, printer, etc.), and memory 822. Input/output interfaces 820 may include a variety of interface units and drives for reading, writing, displaying, and/or printing data or files. Memory 822 may further store operating system software 824 for controlling overall operation of the data server 810, control logic 826 for instructing data server 810 to perform aspects described herein, and other application software 828 providing secondary, support, and/or other functionality which may or may not be used in conjunction with aspects described herein. The control logic may also be referred to herein as the data server software control logic 826. Functionality of the data server software may refer to operations or decisions made automatically based on rules coded into the control logic, made manually by a user providing input into the system, and/or a combination of automatic processing based on user input (e.g., queries, data updates, etc.).

Memory 1122 may also store data used in performance of one or more aspects described herein, including a first database 832 and a second database 830. In some embodiments, the first database may include the second database (e.g., as a separate table, report, etc.). That is, the information can be stored in a single database, or separated into different logical, virtual, or physical databases, depending on system design. Web server 806, computer 804, laptop 802 may have similar or different architecture as described with respect to data server 810. Those of skill in the art will appreciate that the functionality of data server 810 (or web server 806, computer 804, laptop 802) as described herein may be spread across multiple data processing devices, for example, to distribute processing load across multiple computers, to segregate transactions based on geographic location, user access level, quality of service (QOS), etc.

One or more aspects may be embodied in computer-usable or readable data and/or computer-executable instructions, such as in one or more program modules, executed by one or more computers or other devices as described herein. Generally, program modules include routines, programs, objects, components, data structures, etc. that perform particular tasks or implement particular abstract data types when executed by a processor in a computer or other device. The modules may be written in a source code programming language that is subsequently compiled for execution, or may be written in a scripting language such as (but not limited to) HTML or XML. The computer executable instructions may be stored on a computer readable medium such as a nonvolatile storage device. Any suitable computer readable storage media may be utilized, including hard disks, CD-ROMs, optical storage devices, magnetic storage devices, and/or any combination thereof. In addition, various transmission (non-storage) media representing data or events as described herein may be transferred between a source and a destination in the form of electromagnetic waves traveling through signal-conducting media such as metal wires, optical fibers, and/or wireless transmission media (e.g., air and/or space). various aspects described herein may be embodied as a method, a data processing system, or a computer program product. Therefore, various functionalities may be embodied in whole or in part in software, firmware and/or hardware or hardware equivalents such as integrated circuits, field programmable gate arrays (FPGA), and the like. Particular data structures may be used to more effectively implement one or more aspects described herein, and such data structures are contemplated within the scope of computer executable instructions and computer-usable data described herein.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A computer-implemented method comprising:
receiving, via a user interface, a list of two or more target molecules to be identified in a sample for analysis by a mass spectrometry apparatus according to an experimental method defined by a plurality of parameters, wherein the mass spectrometry apparatus is configured to perform the experimental method according to the plurality of parameters to identify the target molecules based at least in part on one or more of a molecular mass, a charge, or a rank intensity of a measurement of the target molecules;
performing a statistical analysis based on the list of two or more target molecules, the statistical analysis configured to determine a probability of misidentifying one or more of the target molecules in the list;
selecting a set of values for the plurality of parameters that reduces the probability below a predetermined threshold value;
configuring the experimental method using the selected set of values for the plurality of parameters; and
operating the mass spectrometry apparatus in accordance with the configured experimental method to analyze the sample for analysis.

2. The computer-implemented method of claim 1, wherein the statistical analysis is performed based on a subset of target molecules in the list, the subset representing a group of relatively less common markers from among the target molecules.

3. The computer-implemented method of claim 1, wherein the plurality of parameters of the experimental method comprise one or more of an elution position, a collisional cross section, a drift position, or a mass accuracy.

4. The computer-implemented method of claim 1, wherein the values for the plurality of parameters are selected based on at least one of:
   a known three-dimensional positioning of one of the target molecules,
   a known fragmentation pattern of one of the target molecules, or
   a known relationship between two of the target molecules.

5. The computer-implemented method of claim 1, further comprising presenting, on the user interface, a score representing a likelihood that a presence or absence of the two or more target molecules will be correctly identified in the sample given the selected set of values.

6. The computer-implemented method of claim 5, wherein the score is computed by:
   (a) consulting a consensus library comprising immutable attributes of spectral features;
   (b) counting a frequency at which one of the target molecules is present in the consensus library;
   (c) transforming the frequency count into a probability score;
   repeating steps (a)-(c) for a plurality of the target molecules; and
   multiplying the probability scores for the plurality of target molecules together.

7. The computer-implemented method of claim 5, wherein the score increases as a function of a number of dimensions of separation available as determined by an acquisition method applied.

8. The computer-implemented method of claim 5, wherein the score increases as a function of a resolving power of the mass spectrometry apparatus.

9. The computer-implemented method of claim 5, wherein the score is computed based on a combination of the two or more target molecules' mass-to-charge ratio, retention time, and drift time.

10. The computer-implemented method of claim 5, wherein the score is computed based on a variability in measurement of a spectrometry standard across a plurality of spectrometry apparatuses.

11. A non-transitory computer-readable storage medium, the computer-readable storage medium including instructions that when executed by a computer, cause the computer to:
   receive, via a user interface, a list of two or more target molecules to be identified in a sample for analysis by a mass spectrometry apparatus according to an experimental method defined by a plurality of parameters, wherein the mass spectrometry apparatus is configured to perform the experimental method according to the plurality of parameters to identify the target molecules based at least in part on one or more of a molecular mass, a charge, or a rank intensity of a measurement of the target molecules;
   perform a statistical analysis based on the list of two or more target molecules, the statistical analysis configured to determine a probability of misidentifying one or more of the target molecules in the list;
   select a set of values for the plurality of parameters that reduces the probability below a predetermined threshold value;
   configure the experimental method using the selected set of values for the plurality of parameters; and
   operate the mass spectrometry apparatus in accordance with the configured experimental method to analyze the sample for analysis.

12. The computer-readable storage medium of claim 11, wherein the statistical analysis is performed based on a subset of target molecules in the list, the subset representing a group of relatively less common markers from among the target molecules.

13. The computer-readable storage medium of claim 11, wherein the plurality of parameters of the experimental method comprise one or more of an elution position, a collisional cross section, a drift position, or a mass accuracy.

14. The computer-readable storage medium of claim 11, wherein the values for the plurality of parameters are selected based on at least one of:
   a known three-dimensional positioning of one of the target molecules,
   a known fragmentation pattern of one of the target molecules, or
   a known relationship between two of the target molecules.

15. The computer-readable storage medium of claim 11, wherein the instructions further configure the computer to present, on the user interface, a score representing a likelihood that a presence or absence of the two or more target molecules will be correctly identified in the sample given the selected set of values.

16. The computer-readable storage medium of claim 15, wherein the score is computed by:
   (a) consulting a consensus library comprising immutable attributes of spectral features;
   (b) count a frequency at which one of the target molecules is present in the consensus library;
   (c) transform the frequency count into a probability score;
   repeating steps (a)-(c) for a plurality of the target molecules; and
   multiply the probability scores for the plurality of target molecules together.

17. The computer-readable storage medium of claim 15, wherein the score increases as a function of a number of dimensions of separation available as determined by an acquisition method applied.

18. The computer-readable storage medium of claim 15, wherein the score increases as a function of a resolving power of the mass spectrometry apparatus.

19. The computer-readable storage medium of claim 15, wherein the score is computed based on a combination of the two or more target molecules' mass-to-charge ratio, retention time, and drift time.

20. The computer-readable storage medium of claim 15, wherein the score is computed based on a variability in measurement of a spectrometry standard across a plurality of spectrometry apparatuses.

21. A computing apparatus comprising:
   a processor; and
   a memory storing instructions that, when executed by the processor, configure the apparatus to:
      receive, via a user interface, a list of two or more target molecules to be identified in a sample for analysis by a mass spectrometry apparatus according to an experimental method defined by a plurality of parameters, wherein the mass spectrometry apparatus is configured to perform the experimental method according to the plurality of parameters to identify the target molecules based at least in part on one or more of a molecular mass, a charge, or a rank intensity of a measurement of the target molecules;

perform a statistical analysis based on the list of two or more target molecules, the statistical analysis configured to determine a probability of misidentifying one or more of the target molecules in the list;

select a set of values for the plurality of parameters that reduces the probability below a predetermined threshold value;

configure the experimental method using the selected set of values for the plurality of parameters; and operate the mass spectrometry apparatus in accordance with the configured experimental method to analyze the sample for analysis.

22. The computing apparatus of claim 21, wherein the statistical analysis is performed based on a subset of target molecules in the list, the subset representing a group of relatively less common markers from among the target molecules.

23. The computing apparatus of claim 21, wherein the plurality of parameters of the experimental method comprise one or more of an elution position, a collisional cross section, a drift position, or a mass accuracy.

24. The computing apparatus of claim 21, wherein the values for the plurality of parameters are selected based on at least one of:

a known three-dimensional positioning of one of the target molecules, a known fragmentation pattern of one of the target molecules, or a known relationship between two of the target molecules.

25. The computing apparatus of claim 21, wherein the instructions further configure the apparatus to present, on the user interface, a score representing a likelihood that a presence or absence of the two or more target molecules will be correctly identified in the sample given the selected set of values.

26. The computing apparatus of claim 25, wherein the score is computed by:

(a) consulting a consensus library comprising immutable attributes of spectral features;

(b) count a frequency at which one of the target molecules is present in the consensus library;

(c) transform the frequency count into a probability score;

repeating steps (a)-(c) for a plurality of the target molecules; and multiply the probability scores for the plurality of target molecules together.

27. The computing apparatus of claim 25, wherein the score increases as a function of a number of dimensions of separation available as determined by an acquisition method applied.

28. The computing apparatus of claim 25, wherein the score increases as a function of a resolving power of the mass spectrometry apparatus.

29. The computing apparatus of claim 25, wherein the score is computed based on a combination of the two or more target molecules' mass-to-charge ratio, retention time, and drift time.

30. The computing apparatus of claim 25, wherein the score is computed based on a variability in measurement of a spectrometry standard across a plurality of spectrometry apparatuses.

* * * * *